United States Patent [19]

Meyers et al.

[11] Patent Number: 4,818,536
[45] Date of Patent: Apr. 4, 1989

[54] EMULSFIABLE POLYMER CONCENTRATE CONTROLLED DELIVERY AND RELEASE SYSTEM

[75] Inventors: Paul A. Meyers, Dublin, Calif.; Linneaus C. Dorman, Midland, Mich.

[73] Assignee: The Dow Chemical Company, Midland, Mich.

[21] Appl. No.: 871,001

[22] Filed: Jun. 5, 1986

[51] Int. Cl.$^4$ ............................................. A01N 25/08
[52] U.S. Cl. ...................... 424/409; 424/78; 424/405; 514/938; 514/475
[58] Field of Search .................. 424/78, 405, DIG. 8, 424/409; 514/475, 938

[56] References Cited

U.S. PATENT DOCUMENTS 3,156,661 11/1964 Feinberg .
3,329,563 7/1967 Sotome ............................. 514/475
4,177,177 12/1979 Vanderhoff et al. ............. 260/29.2
4,282,209 8/1981 Tocker .
4,303,642 12/1981 Kangas ................................. 424/78
4,336,173 6/1982 Ugelstad .
4,460,572 7/1984 Derby et al. ........................ 424/78
4,610,927 9/1986 Igarashi et al. ................. 424/19 X

FOREIGN PATENT DOCUMENTS 1494814 12/1977 United Kingdom .

Primary Examiner—John S. Maples
Attorney, Agent, or Firm—S. Preston Jones; Ronald G. Brookens

[57] ABSTRACT

A storage stable, water emulsifiable, substantially non-aqueous, liquid concentrate adapted for on-site preparation of an aqueous emulsion of an agricultural chemical, consisting essentially of a solution of (a) a hydrophobic agricultural chemical having biocidal activity,
(b) a solid hydrophobic polymer, in an amount effective to achieve sustained release of (a),
(c) a water immiscible organic solvent, and
(d) an emulsifying agent, in an amount effective to form a stable oil-in-water emulsion when the concentrate is mixed with water.

19 Claims, No Drawings

EMULSFIABLE POLYMER CONCENTRATE CONTROLLED DELIVERY AND RELEASE SYSTEM

BACKGROUND OF THE INVENTION

This invention relates to liquid concentrates of agricultural chemicals suitable for the formation of oil-in-water emulsions of a water insoluble biocide therein, more particularly to a stable, emulsifiable concentrate liquid suitable for the controlled delivery of an agricultural biocide after being formed into an aqueous emulsion, and to processes for the manufacture and use thereof.

DESCRIPTION OF THE PRIOR ART

U.S. Pat. No. 4,282,209 is directed to a process for the preparation of controlled release particles of the insecticide methomyl. Initially, methomyl and a polymer, such as polystyrene are dissolved in an organic solvent. The object of the patent is to form particles containing insecticide and the polymer.

U.S. Pat. No. 4,177,177 discloses the direct emulsification of polymers using oil-in-water emulsifiers, polystyrene polymers, a water immiscible solvent which is later removed by evaporation, and extensive mechanical mixing requiring sophisticated equipment, such as is available in a factory or a laboratory, is required.

U.S. Pat. No. 4,336,173 discloses the preparation of an aqueous emulsion or dispersion of a partly water soluble material with an option to futher prepare a polymer dispersion when the dispersed material is a polymerizable monomer.

U.S. Pat. No. 3,167,661 and U.K. Specification No. 1,494,814 are also directed to the preparation of state of the art types of emulsions.

U.K. Pat. No. 1,494,815 discloses the preparation of concentrated resin emulsions for the controlled release and delivery of herbicides wherein such resins are film-forming and hydrophilic, derived from polyurethanes, polyesters or vinylpolymers, which are combined with one or more polyoxyethylene chains.

U.S. Pat. No. 3,156,661 discloses the preparation of latex products comprising dispersed resinous polymeric materials and water composed "predominantly of monomer units such as styrene", wherein the particles dispersed in the aqueous phase contain an insecticide.

In copending U.S. patent application Ser. No. 871,002, filed on June 5, 1986 concurrently with the present application, a storage stable, water emulsifiable, substantially anhydrous, liquid concentrate adapted for on-site preparation of an aqueous emulsion of an agricultural chemical was disclosed consisting essentially of a solution of (a) a hydrophobic agricultural chemical having biocidal activity, (b) a solid hydrophobic polymer, in an amount effective to achieve sustained release of (a), and (c) an emulsifying agent, in an amount effective to form a stable oil-in-water emulsion when the concentrate is mixed with water.

It has been recognized for some time that particulate biocides can be used effectively to control weeds, insects and other pests while, by controlling the rate of release of the biocide, minimizing the undesirable effects of these generally toxic chemicals. However, this basic process is limited in many regards and may require a variety of relatively expensive techniques which are difficult to employ. For example, techniques such as microencapsulation are quite expensive and can lead to the formation of undesirable by-products. Other known methods require tedious control during manufacture and do not always produce the desired end-product. Still other methods require extensive agitation and/or heat, have a short shelf-life, produce products which are not easily storable except under undesirable temperature conditions, etc. Also, it is extremely desirable that a manufactured concentrate be easily mixed with water at the site of application, rather than having to be shipped or transported therewith. Currently, a variety of expensive materials are required in order to mix the biocide-containing composition before it is usable for its intended purpose.

As a result of these problems, there exists a need for economical, easy to handle liquid concentrates which are storage stable, which are easily and readily prepared in a simple container and can be shipped water-free to the end users, e.g., farmers, who can readily mix them with water prior to spraying them onto the sites of application and preferably which impart a sustained release effect to the biocide.

OBJECTS OF THE INVENTION

It is an object of this invention to provide liquid concentrates of agricultural chemicals which readily emulsify when mixed with water. It is another object to provide such concentrates which are substantially non-aqueous apart from the normal water contents of the components thereof, i.e., an aqueous phase is not present therein, thereby rendering them long term storage stable. It is another object to provide such concentrates which can be prepared without heating and extensive stirring or other manner of agitation. It is still another object to provide such concentrates which can be readily formed into stable aqueous emulsions by farmers and other end-users thereof without the necessity of expensive mixing equipment. It is still another object to provide such concentrates which impart a sustained release effect to the agricultural chemical at the sites of application. It is still another object to provide such concentrates which can be readily formed by combining a water immiscible, organic solvent with a liquid or solid agricultural chemical. Other objects will be apparent to those skilled in the art to which this invention pertains.

SUMMARY OF THE INVENTION

In a composition aspect, this invention relates to a storage stable, water emulsifiable, substantially non aqueous liquid concentrate adapted for on-site preparation of an aqueous emulsion of an agricultural chemical, consisting essentially of a solution of (a) a hydrophobic agricultural chemical having biocidal activity (b) a solid hydrophobic polymer, in an amount effective to achieve sustained release of (a), (c) a water immiscible, organic solvent and (d) an emulsifying agent in an amount effective to form a stable oil-in-water emulsion when the concentrate is mixed with water.

In a process aspect, this invention relates to a method of preparing an agricultural concentrate which comprises mixing (a) a hydrophobic agricultural chemical having biocidal activity, with (b) an amount of a solid, hydrophobic polymer in particulate form effective to achieve a sustained release of the agricultural chemical, (c) a water immiscible organic solvent and (d) an emulsifying agent in an amount effective to form a stable oil-in-water emulsion when the concentrate is mixed with water, thereby forming a liquid solution.

In a method of use aspect, this invention relates to a method of imparting a controlled delivery of an agricultural chemical to a locus, comprising the steps of mixing the emulsifiable concentrate consisting essentially of a solution, in (a) a hydrophobic agricultural chemical having biocidal activity, (b) a solid, hydrophobic polymer in an amount effective to form a stable oil-in-water emulsion when the concentrate is mixed with water; with water so as to form an oil-in-water emulsion; and applying the resultant emulsion to the locus.

DETAILED DISCUSSION

The solid polymers which are present in the concentrates of this invention are hydrophobic, i.e., water insoluble, polymers which have a low permeability to water. Such polymers effect the sustained release of the active agricultural agent.

The most preferred polymer, polystyrene, has inherent viscosities between about 0.083 dL/g to 0.44 dL/g, preferbly about 0.18 dL/g to about 0.20 dL/g. These viscosities are based on the relationship between the weight average molecular weight ($\overline{MW}_w$) and the inherent viscosity ($\eta_{Inh}$) at a concentration of 0.100 g/dL in toluene at 25° C.: 1.3914

$$\overline{MW}_w = 3.19 \times 10^3 \eta_{Inh}^{1.3914}$$

Solid polymers which may be utilized and methods of preparing them are well known in the art. Examples of polymers that may be utilized include poly(methyl methacrylate), chlorinated polyethylene and poly(vinyl acetate).

A preferred class of polymers is polystyene and substituted polystyrenes, e.g., substituted in the aromatic ring by lower-alkyl, e.g., methyl, ethyl, tert.-butyl, tert.-amyl, halo, e.g., fluorine, chlorine or bromine, as well as a variety of combinations, multiples and/or mixtures of these. The most preferred polymer is polystyrene.

The polymers employed in the concentrates of this invention must be soluble in the mixture of the agricultural chemical and organic solvent therein, e.g., at least 10% by weight and preferably at least 25% by weight at ambient temperatures. They must also be non-reactive with both the agricultural chemical and organic solvent, i.e., they must be storage stable as a solution therein for at least 6 months and preferably much longer.

The polymer component ordinarily comprises about 10 to 30 wt %, preferably about 25 to 30 wt. %, of the concentrate.

A wide variety of one or more agricultural chemicals, including solid, semi-solid and liquid compositions having biocidal activity can be employed in the concentrates of this invention, e.g., those having insecticidal, fungicidal, pesticidal or herbicidal activity, provided the agricultural chemical is hydrophobic. Examples of such agricultural chemicals are Dowco® 221, (a-(2,2,2-trichloroethyl) styrene); 1,1,1-trichloro-3,4-epoxy-3-phenylbutane; 1,1,1-trichloro-4,5-epoxy-4-(3,5-dichlorophenyl)pentane and 1,1,1-trichloro-4,5-epoxy-4-phenylpentane, tridiphane (Dowco® 356) 1,1,1-trichloro-3,4-epoxy-3-(3,5-dichlorophenyl) butane, and chlorpyrifos(0,0-diethyl 0-3,5,6-trichloro-2-pyridyl phosphorothioate).

Preferred biocides are tridiphane and chloropyrifos.

The biocide component typically is present in the concentrate at a concentration of about 10 to 30 weight percent, most preferably 25 to 30 weight percent.

The oil-in-water emulsifying agent or agents employed in the concentrates of this invention are well-known in the art. Suitable types of emulsifiers are non-ionic surfactants and anionic surfactants.

However, in the broadest embodiment any suitable surface active agent capable of forming stable emulsions of the agricultural chemical-polymer-organic solvent solution may be employed without departing from the spirit and scope of this invention.

Particularly preferred emulsifying agents are those currently sold under the tradenames "Makon 30" and "Makon 14", which are non-ionic alkyl phenoxy polyoxethylene ethanols sold by Stephan Chemical Company, and "Sponto P-10", "20P" and "Sponto 712", which are calcium salts of dodecylbenzene sulfonate, sold by Witco Chemical Co. Mixtures of the surfactants are preferred, but selection is not sharply critical. Some combinations are better than others. Those skilled in the art can make a selection. It is also suitable to use mixtures of emulsifiers.

These emulsifying agents ordinarily are present in the concentrate at a concentration of about 0.5 to 2.0 wt. %, most preferably about 0.7 to 1.3 wt. %.

The organic solvent or solvents suitable for use in the concentrates of this invention are liquids capable of mixing with and forming a resultant homogeneous liquid solution with the agricultural chemical, polymer and emulsifying agent. The solvent should be water immiscible organic. The solvent may be a single liquid compound, or a mixture of two or more. Although substantially non-polar organics such as xylene are typically contemplated, partially polar compounds such as halogenated organics are also suitable. For maximum efficiency and economy, the resulting polymer solution should contain a solid content as high as possible, consistent of course with the required low, dispersible viscosity of the oil-in-water emulsion resulting when mixed with water. Suitable solvent amounts should range from about 35 to 70 wt. %, most preferably about 40 to 50 wt. %. Suitable solvents include the xylenes, toluene, dichloromethane, ethylene dichloride, tetrachloroethylene, tetrachloroethane, and 1,1,1-trichloroethane. The preferred solvent is commerical grade xylene.

The concentrates of this invention are produced by forming a liquid solution of the selected solid polymer, organic solvent, emulsifying agent, and agricultural chemical. This can be accomplished by merely allowing an intimate mixture of the four ingredients to stand for several minutes, hours or days or stirring, or by mixing the first three ingredients to form a liquid concentrate, followed by mixing with the agricultural chemical component to form a homogeneous liquid solution. The formation of the solution can be expedited by mild heating and/or stirring.

Some of the commercially available surfactants contain a small amount of water. Any water in the concentrates greater than about 0.1% can be removed in a separator or with the aid of a solid desiccant like Drierite, which, in turn, can be separated from the concentrates by decantation. These are skills well known to those in the art.

The resulting concentrate of this invention, above its freezing point, is a liquid solution of the polymer, emulsifying agent, agricultural chemical and organic solvent.

Although the essential ingredients of this invention are the hydrophobic agricultural chemical, the hydrophobic polymer, the emulsifying agent and organic solvent, other conventional materials may also be present therein, e.g., one or more complementary and compatible suspending agent, viscosity regulating agents, etc., providing they do not interfere with the function of the four vital components.

In a preferred embodiment, the resulting concentrate is a solution of a liquid agricultural hydrophobic biocide having dissolved therein a solid, hydrophobic polymer and a suitable emulsifying agent, which is mixed with a water immiscible organic solvent, and then mixed with water, preferably at the point of application. The resulting solution forms a stable emulsion, i.e., remains as a single emulsified phase on standing without agitation for at least 30 minutes, preferably at least one hour and more preferably twelve hours or more. The particular polymer and the agricultural chemical used are mutually compatible, with the polymer functioning as a reservior for the controlled release of the agricultural chemical, e.g, biocide, after dispersing by spraying onto the soil. The resulting concentrate is readily prepared by simply combining the ingredients in a single mixing vessel with agitation, but without heat, e.g., at room temperature. Thus, the concentrate is easily and directly distributed, after packaging, to its end users without the burdensome requirement of other preparation steps; e.g., precipitation of the polymer and biocide with a non-solvent under shearing action, drying, grinding and the like. The resulting concentrate has usefully long shelf life being a non-aqueous formulation, and is easily stored under temperature conditions unsuitable for a water-based emulsion, i.e., the concentrate can be stored below the freezing point of water. At the time and place of application, the formulation is mixed with water using simple mixing equipment typically available to farmers, rather than requiring sophisticated or high-speed, heavy mixing equipment which is common to factories or laboratories. In fact, domestic garden hose sprayers or the like can readily be used and since the emulsion is readily prepared at the place of application, the water ingredient does not have to be shipped or transported, thereby resulting in a much lighter product and a significant economic saving. Upon mixing with water, the biocide-containing concentrate is converted into a water-based emulsion, containing the dispersed polymer phase into which is dissolved the biocide. The water-sensitive biocide is stabilized by the surfactant, while the water-sensitive biocide is protected from the water phase. The resulting emulsion is then used as a delivery vehicle for applying the biocide to the situs, e.g., growing plants or soil. Evaporation of the water leaves the biocide in its dispersed polymer reservoir, wherein it is released in a sustained manner to the applied environment, wherein its biological effects are exerted.

The amount of concentrate which is mixed with water is an amount calculated to deliver 0.5 lbs/acre to 2 lbs/acre of active biocide in 2 gal to 100 gal of emulsion. The preferred volume of emulsion to be delivered per acre is 10 gal to 15 gal.

The pests to be so controlled, such as weeds and other undesirables, and the like by applying the particles in any convenient formulation to the locus of infestation, to the area to be protected, or to the pests themselves. Where the control of weeds in agricultural crops is desired, the resulting emulsion is generally applied to the foliage or other plant parts that are to be controlled or to the locus, at a time depending on the mode of action of the particular active ingredient involved. The precise amount to be applied depends on the particular species to be controlled, its life stage, its size and location, the amount of rainfall, the time of year, moisture, temperature, type of application, and other variables known to those in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLES

Formation of Emulsifiable Polymer Concentrate (EPC)

To a mixture of 2 g of polystyrene (Dow, MW 20,000) in a glass bottle was added 2 g of tridiphane, (1,1,1-trichloro-3,4-epoxy-3-(3,5-dichlorophenyl)butane), 4 ml (3.44 g) of xylene and 10 mg of "Makon 14", 27 mg of "Makon 30" and 77 mg of "Sponto P-10-20P". The bottle was capped and the mixture shaken periodically and allowed to stand overnight. The solubilization of the polymer into a homogeneous solution was complete within twenty four hours for all the examples seen in Table I.

The resulting EPC's of Dowco 356 in the remaining examples were prepared by a procedure similar to that above. Surfactants used in preparing the EPC's of herbicide "Dowco 356" were Makon 14 and Makon 30 (Stepan Chemical Company), Sponto® P-10-20P and Sponto® 712 (Witco Chemical Co.) The Makon series are non-ionic alkylphenoxypolyoxyethylene ethanols. The Sponto series are combination non-ionic/ionic calcium salts of dodecylbenzene sulfonate. Polystyrene of varying molecular weights was used, 20,000 (Dow), 30,000 (Polysciences, Inc.), 55,000 (Dow PS 2) and 101,000 (Dow).

Following the above procedure, mixture of polystyrene, "Dowco 356" and surfactant combinations were prepared and evaluated; solution was complete within 24 hours, and the data is set forth in Table I, below.

TABLE I

| Ex. | Surfactant | | Total % | Xylene | | Polystrene | | | Tridiphane | |
|-----|------|-----|-----|-----|-----|-----|-----|-----|-----|-----|
| | Type | (g) | | (g) | % | MW | (g) | % | (g) | % |
| #1 | Makon 30 | 0.027 | 1.5 | 3.4 | 45.5 | 20 M | 2 | 26.5 | 2 | 26.5 |
| | Makon 14 | 0.010 | | | | | | | | |
| | Sponto P-10-20P | 0.077 | | | | | | | | |
| #2 | Makon 30 | 0.029 | 0.7 | 6.9 | 45.9 | 20 M | 4 | 26.7 | 4 | 26.7 |

TABLE I-continued

| Ex. | Surfactant Type | (g) | Total % | Xylene (g) | Xylene % | Polystrene MW | Polystrene (g) | Polystrene % | Tridiphane (g) | Tridiphane % |
|---|---|---|---|---|---|---|---|---|---|---|
|  | Makon 14 | 0.008 | | | | | | | | |
|  | Sponto P-10-20P | 0.069 | | | | | | | | |
| #3 | Makon 30 | 0.027 | 1.3 | 3.4 | 45.7 | 20 M | 2 | 26.5 | 2 | 26.5 |
|  | Makon 14 | 0.005 | | | | | | | | |
|  | Sponto 712 | 0.069 | | | | | | | | |
| #4 | Makon 30 | 0.028 | 0.7 | 6.9 | 45.9 | 20 M | 4 | 26.7 | 4 | 26.7 |
|  | Sponto 712 | 0.073 | | | | | | | | |
| #5 | Makon 30 | 0.027 | 1.4 | 3.4 | 45.6 | 30 M | 2 | 26.5 | 2 | 26.5 |
|  | Makon 14 | 0.009 | | | | | | | | |
|  | Sponto 712 | 0.070 | | | | | | | | |
| #6 | Makon 30 | 0.020 | 0.7 | 6.9 | 45.9 | 30 M | 4 | 26.7 | 4 | 26.7 |
|  | Makon 14 | 0.009 | | | | | | | | |
|  | Sponto 712 | 0.070 | | | | | | | | |
| #7 | Makon 30 | 0.028 | 0.8 | 6.9 | 46.0 | 101 M | 4 | 26.6 | 4 | 26.6 |
|  | Makon 14 | 0.012 | | | | | | | | |
|  | Sponto P-10-20P | 0.069 | | | | | | | | |
| #8 | Makon 30 | 0.026 | 1.3 | 3.4 | 45.6 | 101 M | 2 | 26.5 | 2 | 26.5 |
|  | Makon 14 | 0.007 | | | | | | | | |
|  | Sponto 712 | 0.066 | | | | | | | | |
| #9 | Makon 30 | 0.027 | 0.7 | 6.9 | 45.9 | 101 M | 4 | 26.7 | 4 | 26.7 |
|  | Makon 14 | 0.008 | | | | | | | | |
|  | Sponto 712 | 0.073 | | | | | | | | |
| #10 | Makon 30 | 0.028 | 1.3 | 3.4 | 45.6 | 30 M | 2 | 26.5 | 2 | 26.5 |
|  | Makon 14 | 0.005 | | | | | | | | |
|  | Sponto P-10-20P | 0.070 | | | | | | | | |
| #11 | Makon 30 | 0.026 | 1.3 | 3.4 | 45.6 | 55 M | 2 | 26.5 | 2 | 26.5 |
|  | Makon 14 | 0.006 | | | | | | | | |
|  | Sponto P-10-20P | 0.066 | | | | | | | | |
| #12 | Makon 30 | 0.029 | 0.6 | 6.9 | 46.0 | 30 M | 4 | 26.7 | 4 | 26.7 |
|  | Makon 14 | 0.006 | | | | | | | | |
|  | Sponto P-10-20P | 0.059 | | | | | | | | |
| #13 | Makon 30 | 0.029 | 0.7 | 6.9 | 45.9 | 30 M | 4 | 26.7 | 4 | 26.7 |
|  | Makon 14 | 0.008 | | | | | | | | |
|  | Sponto P-10-20P | 0.077 | | | | | | | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A storage stable, water emulsifiable, substantially non-aqueous liquid or low melting solid concentrate having a water content not greater than about 0.1% which is adapted for use in the on-site preparation of an aqueous emulsion of an agricultural chemical, consisting of a solution of
    (a) at least one liquid hydrophobic agricultural chemical having bicidal activity from the group consisting of (α-(2,2,2-trichloroethyl)styrene); 1,1-trichloro-3,4-epoxy-3-phenylbutane; 1,1,1,-trichloro-4,5-epoxy-4-(3,5-dichlorophenyl)pentane; 1,1,1-trichloro-4,5-epoxy-4-phenylpentane; 1,1,1-trichloro-3,4-epoxy-3-(3,5-dichlorophenyl) butane and O,O-diethyl O-3,5,6-trichloro-2-pyridylphosphorothioate,
    (b) a solid hydrophobic polymer, in an amount effective to achieve sustained release from the concentrate of the compound of (a),
    (c) a water immiscible organic solvent, and
    (d) an emulsiying agent, in an amount effective to form a stable oil-in-water emulsion when the concentrate is mixed with water.

2. A method for the controlled delivery of an agricultural chemical to a locus, comprising
    mixing the emulsifiable concentrate of claim 1 with water so as to form an oil-in-water emulsion; and applying the resulting emulsion to the locus.

3. A concentrate as claimed in claim 1 wherein the concentrate is a liquid at ambient temperature.

4. A concentrate as claimed in claim 3 wherein the agricultural chemical is present in the concentrate in an amount of about 10 to 30 wt. %.

5. A concentrate as claimed in claim 4, wherein the organic solvent is selected from the xylene, toluene, dichloromethane, ethylene dichloride, tetrachloroethylene, tetrachloroethane, 1,1,1-trichloroethane or mixtures thereof.

6. A concentrate as claimed in claim 5, wherein the organic solvent is xylene.

7. A concentrate as claimed in claim 5 wherein the hydrophobic polymer is polystyrene, a substituted polystyrene, or a mixture thereof.

8. A concentrate as claimed in claim 7 wherein the emulsifying agent is an anionic surfactant.

9. A concentrate as claimed in claim 7 wherein the polymer is polystyrene.

10. A concentrate as claimed in claim 9 wherein the polymer is present in the concentrate in an amount of about 10 to 30 wt. %.

11. A concentrate as claimed in claim 7, wherein the polymer is soluble in the mixture of the agricultural chemical and solvent in an amount of at least 10% by weight.

12. A concentrate as claimed in claim 11, wherein the polymer is soluble in the mixture of the agricultural chemical and solvent in an amount of at least 25% by weight.

13. A concentrate according to claim 8 wherein the agricultural chemical is α-(2,2,2-trichloroethyl)styrene.

14. A concentrate according to claim 8 wherein the agricultural chemical is 1,1,1-trichloro-3,4-epoxy-3-phenylbutane.

15. A concentrate according to claim 8 wherein the agricultural chemical is 1,1,1-trichloro-4,5-epoxy-4-(3,5-dichlorophenyl)pentane.

16. A concentrate according to claim 8 wherein the agricultural chemical is 1,1,1-trichloro-4,5-epoxy-4-phenylpentane.

17. A concentrate according to claim 8 wherein the agricultural chemical is 1,1,1-trichloro-3,4-epoxy-3-(3,5-dichlorophenyl)butane.

18. A concentrate according to claim 8 wherein the agricultural chemical is 0,0-diethyl 0-3,5,6-trichloro-2-pyridylphosphorothioate.

19. A method of forming a storage stable, water emulsifiable, substantially non-aqueous concentrate which comprises mixing
 (a) at least one liquid hydrophobic agricultural chemical haivng biocidal activity from the group consisting of (α-(2,2,2-trichloroethyl)styrene); 1,1,1-trichloro-3,4-epoxy-3-phenylbutane; 1,1,1-trichloro-4,5-epoxy-4-(3,5-dichlorophenyl)pentane; 1,1,1-trichloro-4,5-epoxy-4-phenylpentane; 1,1,1-trichloro-3,4-epoxy-3-(3,5-dichlorophenyl) butane and 0,0-diethyl 0-3,5,6-trichloro-2-pyridylphosphorothioate,
 (b) a solid hydrophobic polymer, in an amount effective to achieve sustained release from the concentrate of the compound of (a),
 (c) a water immiscible organic solvent, and
 (d) an emulsifying agent, in an amount effective to form a stable oil-in-water emulsion when the concentrate is mixed with water.

* * * * *